United States Patent [19]
Hoberman

[11] Patent Number: 5,159,934
[45] Date of Patent: Nov. 3, 1992

[54] MINIATURE SENSOR FOR MAINSTREAM CAPNOMETRY/CAPNOGRAPHY INSTRUMENTATION

[76] Inventor: Max Hoberman, 943 Prince St., Teaneck, N.J. 07666

[21] Appl. No.: 579,561

[22] Filed: Sep. 10, 1990

[51] Int. Cl.$^5$ .............................................. A61B 5/08
[52] U.S. Cl. ...................................... 128/719; 422/84
[58] Field of Search ....................... 128/716, 719, 730; 422/84

[56] References Cited

U.S. PATENT DOCUMENTS

| | | | |
|---|---|---|---|
| 4,648,396 | 3/1987 | Raemer | 128/719 |
| 4,649,027 | 3/1987 | Talbot | 128/719 |
| 4,707,336 | 11/1987 | Jones | 128/719 |
| 4,914,720 | 4/1990 | Knodle et al. | 128/719 |
| 4,955,946 | 9/1990 | Mount et al. | 128/719 |
| 4,958,075 | 9/1990 | Mace et al. | 128/719 |
| 5,022,406 | 6/1991 | Tomlinson | 128/730 |

FOREIGN PATENT DOCUMENTS 0385256  9/1990  European Pat. Off. ............ 128/719

Primary Examiner—Lee S. Cohen
Assistant Examiner—K. M. Pfaffle

[57] ABSTRACT

This invention relates to sensors for Capnometry or Capnography applications wherein measurement is made on the mainstream of the patients breathing tube gases. Provision is made for sampling the respired gases and periodically stopping them off from the sensing mechanism while introducing instead, gases of known concentrations into the sensing cell for calibrating purposes. Several methods are described for activating the valving mechanism included in the miniature sensor. In principle this invention overcomes the time delay and complexity inherent in side-stream Capnometry/Capnography where rapid, up-to-date readings of $CO_2$ concentration in the patients air stream are delayed due to the length of the sampling tube to the measuring instrument by reversing the process and carrying calibration gases which need not change rapidly to the main-stream sensor where they can be periodically sampled and thus not impairing the higher speed response possible with main-stream sensing systems.

7 Claims, 3 Drawing Sheets

MINIATURE SENSOR FOR MAINSTREAM CAPNOMETRY/CAPNOGRAPHY INSTRUMENTATION

BACKGROUND OF THE INVENTION

Carbon dioxide monitoring of patients respired gases, during anesthesia and the display of its numerical value is referred to as Capnometry and Capnography, the system which adds a graphic display of the instantaneous concentration of carbon dioxide, is now generally accomplished by using non-dispersive Infra-red or IR Spectrometry techniques. Two broad classes of measurement systems have been developed:

(a) The first, side-stream monitors, is the type where the measurement is performed in the IR monitor upon a sample of gas.

This sample of gas is continuously drawn from the patients airway by means of a suction pump. The suction pump is connected by way of a small diameter tube to a T-piece, placed on the tracheal tube; anesthesia mask connector; or through a tube introduced into the pharynx through the patient's nostril. Compensation or scavenging must be provided in the carbon dioxide monitor to prevent spurious readings due to the effects of atmospheric pressure; halogenated anesthetic vapors; nitrous oxide; and/or water vapor. However another and a greater source of error or malfunction is due to the clogging of the tubing necessary to convey the sample gas from the patient to the monitoring instrument. In practice, it is desirable that this tubing be a small diameter capillary tube to minimize "dead volume". The "dead volume" is the volume of gas in the tubing between the sampling tube and monitor or measuring device. This "dead volume" must be completely displaced to update the instantaneous measurements. During the displacement of the "dead volume", this tubing becomes susceptible to clogging and/or occlusion due to condensed water vapors and/or patient secretions.

In some monitors or devices, an alarm is sounded when clogging becomes excessive. Compensating corrections in some instruments may take the form of either reversing air-flow to clear moisture or secretions out of the tubing, or increasing of the sample flow to act as a purge. However, since side-stream instruments have ample room within them, scavenging, liquid traps, calibration and compensation means can be readily incorporated at the cost of slower response time, while not reducing the risk of clogging in the long sampling tube. In addition, the patients breath and secretions drawn into the instrument may come into contact with the permanent pneumatic components and thus pose a possibility of cross-contamination between patients which then must be dealt with.

(b) The second class of $CO_2$ monitor, the main stream type, incorporates a special breathing circuit insert (cuvette) for attaching the IR sensor to the Y-piece of the breathing circuit.

This main stream type directs the IR from an IR source or sources, of an appropriate wavelength, to pass directly through the airway where its intensity is attenuated by the gas concentration and measured at the opposite end of the breathing tube. While this second class of $CO_2$ monitor provides a faster and more direct reading of the gas concentration then the side-stream type instruments, it also presents another problem. The problem of the main-stream type instrument is the need to incorporate an IR source and detector in addition to the compensation and calibration circuitry into the device itself. This device which is unsupported, may significantly increase the traction placed on the patients airway by the tracheal tube and therefore making for a complicated and expensive sensing device.

DESCRIPTION OF THE PRIOR ART

The measurement of the respired gases, particularly $CO_2$, has developed to mature commercial products as evidenced by the enclosed bulletins of the Novametrix Mainstream Capnograph. A search of related patents disclosed several pertinent to the invention described here. This includes Application No. 55-99495 of Kurahashi which utilizes a chopper mechanism for drift compensation and correction which the present invention, and subject of the application is intended to eliminate.

Also of note, is the Gas detector described in the Abstract of the EMI Ltd Patent No. 1398977. The EMI Ltd. device includes a tungsten filament source with a selective IR filter and a lead selenide detector as therein described. It is to be noted that again a filter wheel is required when a single detector is used, and which the present invention and application eliminates.

Also of note is the Gas Analyzer as disclosed by Shigiyama, in Kokai No. 52-122172. Shigiyama describes a device with a single light source without a mechanical chopper, wherein calibration is obtained when introducing only $N_2$ gas. No valve system is described for use in miniature mainstream respired gas instrumentation.

Also of note is the Infrared absorption type Gas Alarming Device, Kokai No. 54-5777 of Yoshihido Okuda, which utilizes a chopper mechanism for achieving stability by comparing the output of the radiation attenuated by the absorbing gas with a reference voltage and restoring them to equality by varying the current in the source of IR, thus achieving stable operation. Since a chopper mechanism is required for calibration, unlike the device described in the present application where no chopper is necessary, a significant difference exists.

Also noted is the gas Cell of a Heated Type, and the subject of the Keigo Nakamura Application No. 54-143128. Nakamura includes a detecting cell with a surrounding heater mechanism. This arrangement is provided to reduce the effect of water vapor condensation which leads to a lower transmission rate in an IR measuring system. While such a heater would be a useful addition to the device in the present application, its use is not claimed.

Also noted is the Gas Analyzer, as disclosed in Shigiyama Kokai No. 52-115279, for a simple gas analysis cell which uses a single IR source and a single detector. Calibration is again performed by the introduction of $N_2$ gas in the absence of the gas to be measured in order to obtain a fixed reference value.

The causes of calibration change of sensors used in Capnography and Capnometry (hereinafter described by the general term "Capnometry") can be divided into two categories:

(a) Those due to long term effects such as deterioration in radiated IR intensity, detector sensitivity, and changes in electronic gain and scale factor which may occur with aging; and (b) the second category; short term effects which include fogging due to condensation, atmospheric pressure changes, changes in the rate of flow of gas mixtures and sudden instrument malfunctions. Since an instrument which is operative and properly adjusted at the beginning of a procedure may be expected to maintain its calibration settings over at least a short period of time, calibration checks need not be performed more often than necessary to correct for possible changes nor as needed to preclude danger to the patient. In recognition of this, a considerable reduction in sensor complexity can be achieved which will reduce the instrument cost and significantly increase its accuracy and reliability by performing calibration checks with primary gas standards of known composition for zero and span settings and any intermediate mixtures desired only at such times as deemed necessary, rather than at a high chopping rate. This miniature sensor would particularly be useful with Mainstream Capnometry monitors.

SUMMARY OF THE INVENTION

It is a purpose of this invention to provide a simple, lightweight sensor/cuvette assembly for mainstream $CO_2$ monitoring by minimizing the instrumentation contained therein while adapting to it some of the calibration and standardization features which can ordinarily be incorporated only into larger side-stream units. In that respect it might be termed a "micro-sidestream" mainstream sensor.

In principle, the sensor consists of an arrangement of an IR source, a sampling cell, and an IR detector arrangement. This improved sensor is adapted for passing $CO_2$ specific radiation through the sampling cell, into which is alternately introduced the gases from the patient's breathing tube and or, alternatively, the known gases for calibration purposes. The calibration of the monitor is accomplished by selectively and periodically operating an integral valve mechanism. This valve mechanism blocks the access or communication between the sampling cell and the breathing tube while simultaneously opening passages of the valve mechanism to introduce $CO_2$ free reference gases. These reference gases, obtained from the instrument package, are introduced into the sampling cell for the purpose of enabling the automatic setting of the instrument to zero. Alternatively, it is possible to introduce a reference gas, from the instrument package, at a known $CO_2$ concentration for calibrating the instrument to any specific span, as may be desired.

The techniques of signal processing of the electrical output of the solid-state IR sensors or detectors are well known in the art and so are not described as part of this present invention. This present invention is primarily directed to the transducer-sensor portion of a complete Capnometry system for detecting changes in the intensity of IR radiation. The changes in intensity of IR radiation is caused by their absorption in the breathing or calibrating gas. The changes in intensity is converted into an electrically varying signal which is transmitted to a monitor or instrument. This invention is directed in particular, to a simple means for accurately calibrating such a sensor, periodically, during its use.

DESCRIPTION OF THE PREFERRED EMBODIMENT

Figure 1:
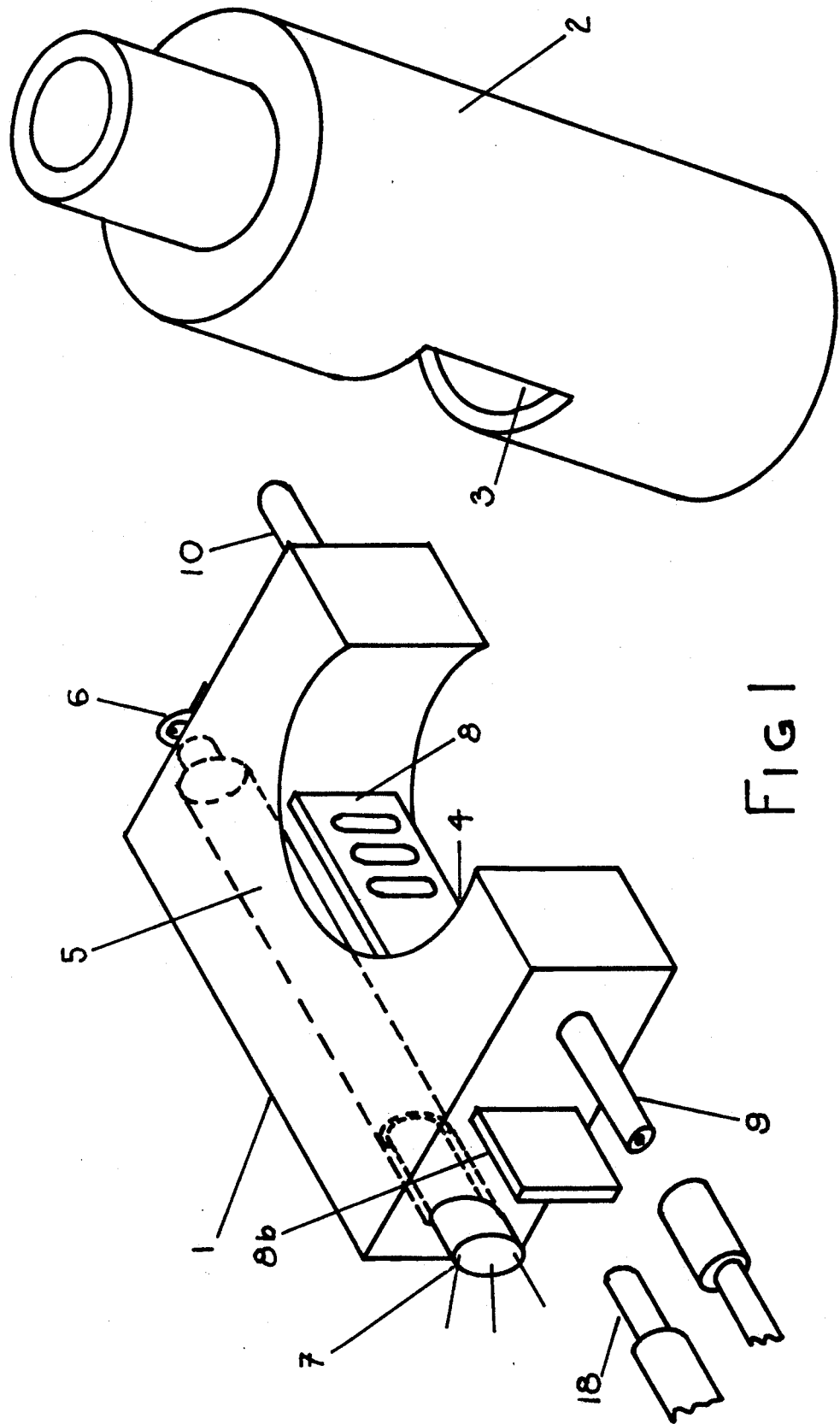
FIG. 1 is an exploded isometric view of the sensor and airway adapter depicting the IR source, sampling cell, IR detector, valve mechanism and input and output ports for calibration gases.

Referring to FIG. 1, there is shown a view of the miniature IR Capnometry sensor, identified as 1 adapted for mounting juxtaposed to an airway adapter 2. The airway adapter 2 forms a section of a breathing tube as used in the application of anesthetic gases, to a patient, during surgery. This airway adapter 2 includes a cutout section 3 into which a partially circularly cutout portion 4 of the IR sensor 1 snugly fits. The sensor 1 is held in a selected position with the airway adapter 2 of the breathing tube by the clamping action of the partially circular portion 4. It is anticipated that partially circular portion 4 will be formed with somewhat more than an included arc of 180 degrees. Sensor 1 includes a cylindrical sampling cell 5, which is fitted at one end with an infra-red source 6, specific to $CO_2$, and a solid state IR detector 7 at its distal and opposite end. One wall of the sampling cell 5 is cut and a sliding valve mechanism 8 is arranged in sensor 1, so as to provide a valve means between the sampling cell 5 and the airway adapter 2 when sensor 1 is inserted into cutout section 3.

Sensor 1 is also provided with an inlet port 9 adapted for the introduction of calibration gases into the sampling cell 5 and an exit port 10 for exhausting the calibration gases during the calibration procedure. A mechanical actuator 18 is aligned with an extended portion 8b of the sliding valve mechanism 8 in longitudinal position. The mechanical actuator 18 is adapted to operate the sliding valve mechanism 8 for calibration purposes.

Figure 3B:
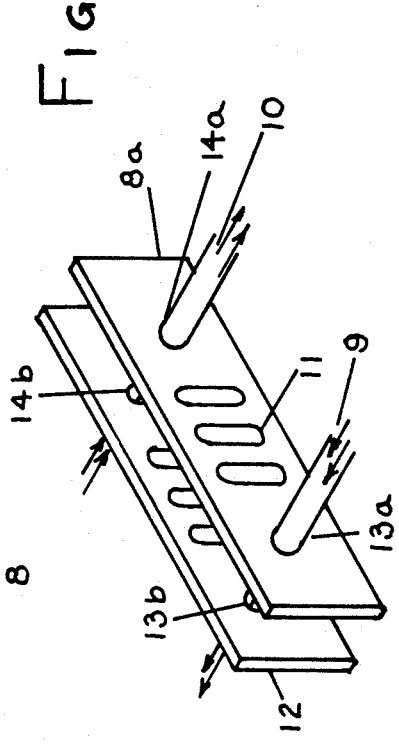
FIG. 3B depicts a fragmentary exploded view of the sensor valve mechanism, this view particularly showing access blocked for the airway adapter gases and open to the calibration gases.
Figure 3A:
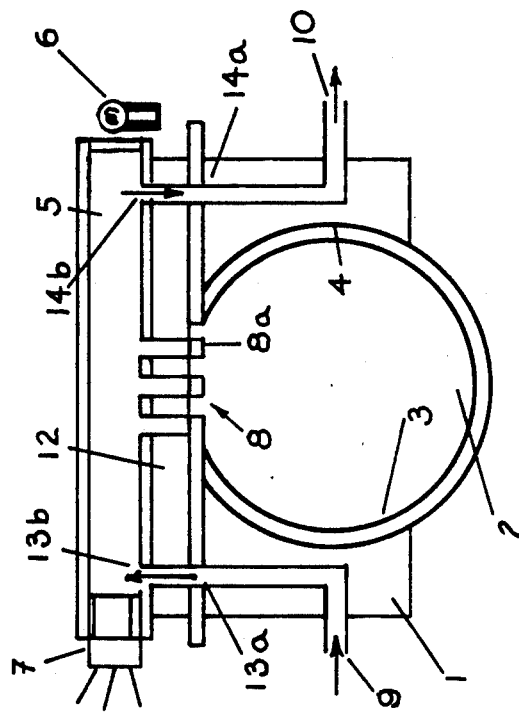
FIG. 3A depicts a cross-sectional view, partly schematic, of the sensor in its calibration state, and showing in particular the access blocked for the gases of the airway adapter and the valve mechanism operated for introducing calibration gases into the sampling cell and discharging them.
Figure 2B:
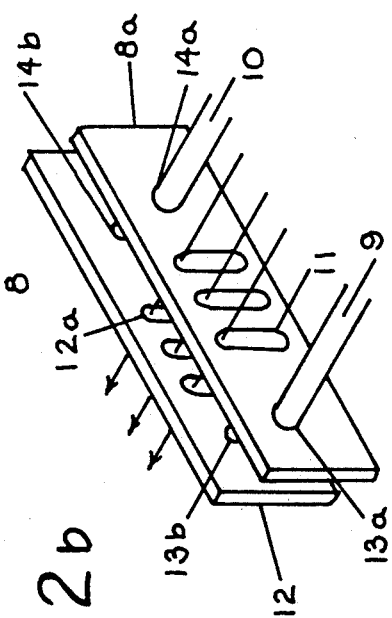
FIG. 2B depicts a fragmentary exploded view of the sensor valve mechanism, this view particularly showing the arrangement of components and access to the sampling cell for the gases of the airway adapter.
Figure 2A:
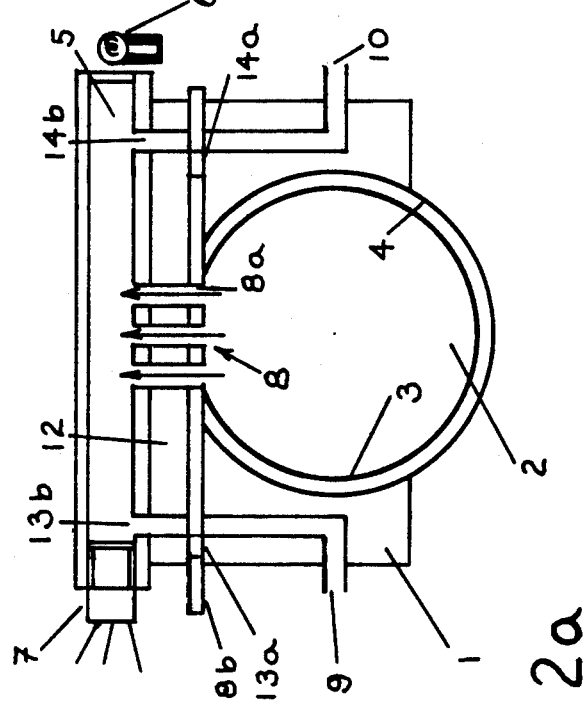
FIG. 2A depicts a cross-sectional view, partly schematic, of the sensor in its normal operating position and showing the access of the gases of the airway adapter to the sampling cell.

Operation of the Capnometry sensor is detailed in FIG. 2A, a cross-section view, when in its normal operating position and FIG. 3A, when in its calibration mode. FIGS. 2B and 3B depict exploded views of the sliding valve mechanism 8 and corresponding to the cross-section view of FIGS. 2A and 3A, where corresponding parts bear the same number designation in all figures.

The sliding valve mechanism 8 consists of a sliding portion 8a containing a series of spaced slotted apertures 11 and two circular apertures 13a and 14a respectively. This sliding portion 8a is selectively positioned against a stationary flattened portion 12 of the sampling cell 5. The flattened portion 12 is provided with slotted apertures 12a which are spaced and similarly shaped to apertures 11. A second set of apertures 13b and 14b are also formed in the flattened portion 12 in a selected position. Apertures 13b and 14b are selectively displaced in longitudinal position so that in one extreme operating position of the valve mechanism 8, the normal operating position, the slots 11 in sliding portion 8a are in alignment with the slots 12a of the flattened portion 12. In the normal operating position hole pairs 13a and 13b and hole pairs 14a and 14b are displaced from each other. In the other extreme position of the sliding valve mechanism 8, the slotted apertures 11 of the sliding portion 8a are displaced with respect to the corresponding slots 12a in the flattened portion 12, while the hole pairs 13a, 13b, and 14a, and 14b are then aligned. In normal operation of the sliding valve mechanism 8 of the sensor 1 (FIGS. 2A and 2b), the alignment of the slots 12a and 11 in the flattened portion 12 and sliding portion 8a of the valve mechanism 8 allow gases from the airway adapter 2 to enter the sampling cell 5. IR, specific to $CO_2$, from the IR source 6 is directed through the sampling cell 1 where it is absorbed in proportion to its concentration and then its intensity is measured by the solid state detector 7.

When calibration is to be performed, the mechanical actuator 18 of FIG. 1 is operated, moving the sliding portion 8a of the sliding valve mechanism 8 to the calibration or extreme position (FIGS. 3A and 3B). This calibrating or extreme position displaces the alignment of slots 12a and slots 11 in the flattened portion 12 and sliding portion 8a of the valve mechanism 8, while simultaneously aligning the hole pairs 13a with 13b and 14a with 14b, permitting the introduction of calibration gases from the input port 9 into the sampling cell 5 and their exit through exit port 10.

The sliding arrangement of the valve mechanism 8 is a preferred construction, since sliding motion provides a wiping action which helps in cleansing the ports of patient secretions and foreign matter, although other constructions will be apparent to one skilled in the arts.

Depicted in FIG. 1 is a valve mechanism 8 which is operated mechanically by an actuator 18. It is anticipated that the actuator 18 may be a thin diameter flexible cable or catheter as used in medical procedures, in order to minimize size and weight.

DESCRIPTION OF FIG. 4 AND FIG. 5

Figure 4:
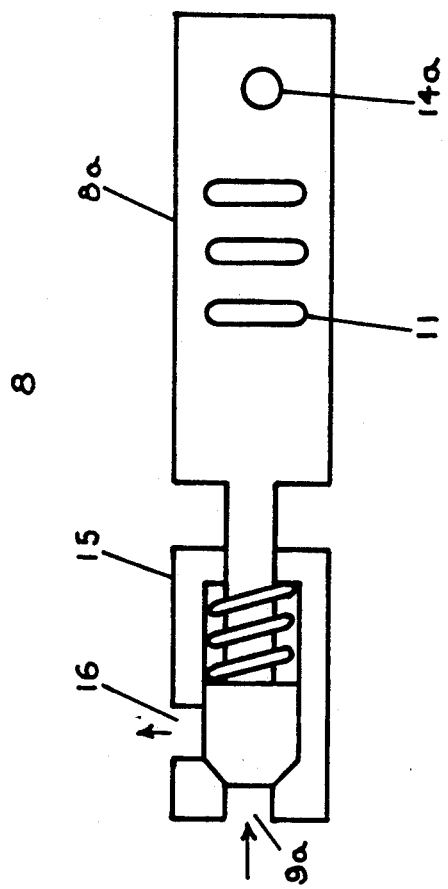
FIG. 4 depicts a first alternate embodiment of a valve mechanism which utilizes the calibration gas pressure to actuate the valve mechanism for operating the ports between the airway adapter and the ssampling cell.

The construction shown in FIG. 4 depicts a first alternate mechanism for operating the sliding portion valve 8a by and with the calibrating gas pressure itself. Referring to FIG. 4, calibration gas entering input port 9a operates a spring loaded plunger 15 to uncover a port 16 admitting the calibrating gas into the sampling cell 5 (not shown in this Figure but previously described). In this case the entry port 9a and the port 16 replace the holes 13a and 13b of the preferred embodiment. Operation is otherwise similar to that previously described.

Figure 5:
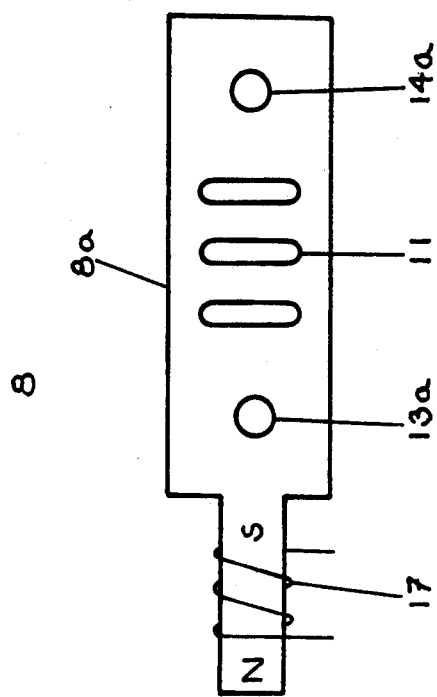
FIG. 5 depicts a second alternate embodiment of a valve mechanism which utilizes a miniature solenoid for actuating the valve mechanism for operating the ports between the airway adapter and the sampling cell.

FIG. 5 depicts a second alternative arrangement where the displacement of the sliding portion 8a of the valve 8 is accomplished by a miniature electrical solenoid 17.

The IR source shown as 6 in the various figures may be of the specific frequency type, generating IR by the high frequency-high voltage excitation of $CO_2$ at low pressure in a sealed tube or may be a black body source filtered by an appropriate filter (not shown in the figure) to provide IR at the $C^{12}O_2$ wavelength in a range between 4.3-4.35 microns. The use of an IR source of either the specific frequency type described above or the black body type with filter operating at the wavelength of $C^{13}O_2$ thereby partially detuned from the wavelength of $C^{12}O_2$ which the patient essentially respires, allows the use of a longer sampling cell 5 which is desirable in some cases from mechanical considerations. I have found that an incandescent bulb such as the standard type 55 operated at below the specific operating voltage of 7 volts from a "soft" source (one which does not shock the lamp filament with suddenly applied voltages) and with pulses of substantially triangular or trapezoidal waveform, will give thousands of hours of operation as a simple, cheap, readily replaceable "black body" source.

The detector may be of the pyroelectric or lead-salt type, depending upon whether the slower response time of the former is adequate for Capnometry purposes or the latter required for its higher response time as necessary for Capnography.

The foregoing discussion is merely illustrative of the principles of the present invention and there are anticipated many modifications, changes and adaptations thereof which will become apparent to those skilled in the art without departing from the scope and spirit of the present invention and while it has been described chiefly with reference to the measurement of carbon dioxide in a patient's respired gases, it is readily adaptable to the measurement of other gases utilizing the same principles of measurement and calibration herein described.

What is claimed is:

1. A miniature IR sensor for use in main-stream Capnometry/Capnography instrumentation, comprising:
   (a) a breathing tube;
   (b) an assembly including a first inlet port, a second exit port, and a third port in said assembly, said third port arrayed in and through a wall portion of said assembly and communicating with said first inlet port and second exit port, said assembly attached in series with said breathing tube carrying breathing gases for evaluation by said miniature IR sensor;
   (c) a partially circular cutout portion in said assembly fitting onto and into said breathing tube and providing a substantially air tight connection therewith;
   (d) a sampling cell formed interior of said assembly;
   (e) a source of infra-red radiation mounted at a first end of the sampling cell, said infra-red source arrayed for passing said radiation into said sampling cell;
   (f) an infra-red detector means mounted at a second end of said sampling cell, said second end distal and opposite said first end, said infra-red detector means for detecting said radiation emerging from the sampling cell;
   (g) a valve member mounted integrally within said assembly, said valve member arrayed immediately adjacent a wall of said sampling cell, said valve member including:
   (g1) said first inlet port for fluidly connecting a source of calibrating gases with the sampling cell;

(g2) said second exit port for fluidly connecting said sampling cell with an exhausting means for exhausting said calibrating gases;

(g3) a plurality of elongated passageways fluidly connecting said breathing gases in said breathing tube with said sampling cell;

(g4) an extended portion means of said valve member moving said valve member from a first normal operating position to a second calibrating position;

(h) an actuating means for engaging said extended portion means of said valve member, said actuating means arranged for selectively moving said extended portion means and valve member between said first normal operating position and said second calibrating position; said first normal operating position allowing only the breathing gases carried in said breathing tube to enter said sampling cell, and said second calibrating position allowing said calibrating gases to enter said sampling cell and excluding said breathing gases from entering said sampling cell, said second calibrating position allowing said calibrating gases to be exhausted from said sampling cell.

2. A miniature IR sensor for use in main-stream Capnometry/Capnography instrumentation as recited in claim 1 wherein said actuating means is a flexible cable, said flexible cable reciprocally moving said valve means between said first normal operating position and said second calibrating position.

3. A miniature IR sensor for use in main-stream Capnometry/Capnography instrumentation as recited in claim 1 wherein the actuating means comprises a bearing member, a plunger slidably carried in said bearing member and a biasing means for selectively positioning said plunger in said bearing member and allowing said calibrating gases to urge said plunger to the said calibrating position, said second calibrating position of said plunger placing said valve member into said second calibrating position.

4. A miniature IR sensor for use in main-stream Capnometry/Capnography instrumentation as recited in claim 1 wherein said actuating means is an electromechanical solenoid.

5. A miniature IR sensor for use in main-stream Capnometry/Capnography instrumentation as recited in claim 1 wherein said source of infra-red radiation is of a specific frequency of wavelength between 4.3 and 4.35 microns.

6. A miniature IR sensor for use in main-stream Capnometry/Capnography instrumentation as recited in claim 1 wherein said source of IR radiation is a black body type.

7. A miniature IR sensor for use in main-stream Capnometry/Capnography instrumentation as recited in claim 6 wherein said black body type source of IR radiation further includes:

(a) a tungsten filament bulb energized with pulses of substantially triangular or trapezoidal waveform;

(b) a filter means to filter said radiation emitting from said tungsten filament bulb to within a wavelength range between 4.3 and 4.35 microns.

* * * * *